United States Patent [19]

Bountra et al.

[11] Patent Number: 5,719,185
[45] Date of Patent: Feb. 17, 1998

[54] USE FOR GABA AGONISTS FOR TREATING EMESIS

[75] Inventors: Charanjit Bountra, Herts; David Edmund Bays, Hertfordshire, both of Great Britain

[73] Assignee: Glaxo Group Limited, London, England

[21] Appl. No.: 532,813
[22] PCT Filed: Apr. 21, 1994
[86] PCT No.: PCT/EP94/01319
 § 371 Date: Oct. 23, 1995
 § 102(e) Date: Oct. 23, 1995
[87] PCT Pub. No.: WO94/25016
 PCT Pub. Date: Nov. 10, 1994

[30] Foreign Application Priority Data

Apr. 23, 1993 [GB] United Kingdom ............. 9308430

[51] Int. Cl.⁶ .................................................. A61K 31/195
[52] U.S. Cl. ................................................... 514/567
[58] Field of Search ...................................... 514/567

[56] References Cited

U.S. PATENT DOCUMENTS 5,091,184 2/1992 Khanna .................................. 424/435

FOREIGN PATENT DOCUMENTS 0 356 128 2/1990 European Pat. Off. .

OTHER PUBLICATIONS

Dickson et al., *The Lancet*, 23 Jul. 1983, p. 227.
Hillier, R., *British Medical Bulletin*, vol. 46, No. 1, 1990, pp. 271–291.
Hanks et al., *The Lancet*, vol. 339, 25 Apr. 1992, pp. 1031–1036.
Wyant, *Drugs*, vol. 26, 1983, pp. 262–267.

*Primary Examiner*—Raymond Henley, III
*Attorney, Agent, or Firm*—Bacon & Thomas

[57] ABSTRACT

The present invention relates to the use of GABA agonists having an agonist action at $GABA_B$ receptors in the treatment of emesis.

15 Claims, No Drawings

USE FOR GABA AGONISTS FOR TREATING EMESIS

This is a 371 of PCT/EP94/01319 filed Apr. 21, 1994.

The present invention relates to the use of γ-aminobutyric acid (GABA) agonists having an agonist action at $GABA_B$ receptors in the treatment of emesis.

GABA is an endogenous inhibitory neurotransmitter in the CNS and peripheral nervous systems. Receptors for GABA have been divided into $GABA_A$ and $GABA_B$ receptor sub-types. $GABA_B$ agonists are described as being of use in the treatment of CNS disorders, such as muscle relaxation in spinal spasticity, cardiovascular disorders, asthma, gut motility disorders such as irritable bowel syndrome and as prokinetic and anti-tussive agents.

It has now been found that GABA agonists having an agonist action at $GABA_B$ receptors are useful in the treatment of emesis.

The invention accordingly provides, in a first aspect, the novel use of GABA agonists having an agonist action at $GABA_B$ receptors in the treatment of emesis.

There is also provided as a further aspect of the invention the use of GABA agonists having an agonist action at $GABA_B$ receptors in the preparation of a medicament for use in the treatment of emesis.

In an alternative or further aspect there is provided a method for the treatment of a mammal, including man, suffering from or susceptible to emesis, comprising administration of an effective amount of a GABA agonist having an agonist action at $GABA_B$ receptors.

There is an isolated report (*The Lancet*, Jul. 23, 1983, pg. 227) that baclofen reduced the frequency of vomiting due to duodenal ileus in a patient with Duchenne muscular dystrophy. It is submitted that the use of (±) baclofen in the treatment of emesis caused by duodenal ileus is not included within the scope of the instant invention.

Thus, according to a further aspect the invention provides the use of GABA agonists having an agonist action of $GABA_B$ receptors in the treatment of emesis with the proviso that, when the emesis is caused by duodenal ileus, the GABA agonist is other than (±) baclofen.

It will be appreciated that reference to treatment is intended to include prophylaxis as well as the alleviation of established symptoms.

GABA agonists having an agonist action at $GABA_B$ receptors have been shown to have anti-emetic activity as indicated by for example their ability to inhibit emesis induced by a variety of emetogens in the ferret.

The treatment of emesis mentioned hereinbefore includes the treatment of nausea, retching and vomiting. Emesis includes acute emesis, delayed emesis and anticipatory emesis. GABA agonists having an agonist action at $GABA_B$ receptors are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis; pregnancy; vestibular disorders, such as motion sickness or vertigo; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); and opioid analgesics, such as morphine.

Specific GABA agonists having an agonist action at $GABA_B$ receptors for use in the present invention include 4-amino-3-(5-chloro-2-thienyl)butyric acid and those compounds generically and specifically disclosed in GB 1017439, e.g. baclofen, U.S. Pat. No. 4,656,298, e.g. 3-aminopropylphosphonous acid (3-aminopropylphosphinic acid), EP 0356128, i.e. 3-(aminopropyl)methyl phosphinic acid, and EP0463969, e.g. 3-(2-imidazolyl)-4-aminobutanoic acid which disclosures are incorporated herein by reference. A particularly preferred compound for use in the present invention is baclofen.

Baclofen, when used in the present invention, may be in the form of a mixture of isomers, for example a racemic mixture, or a separated isomer, i.e. the S(+) isomer or R(−) isomer. Preferably the R(−) isomer of baclofen is used.

$GABA_B$ agonists may be administered as the raw chemical but are preferably presented as a pharmaceutical formulation. Suitable pharmaceutical formulations for $GABA_B$ agonists are described in the art.

For example $GABA_B$ agonists may be formulated for oral, buccal, parenteral, depot or rectal administration or in a form suitable for administration by inhalation or insufflation (either through the mouth or nose). Oral and parenteral formulations are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The $GABA_B$ agonists may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents.

Alternatively, the active ingredient may be in powder form for constitution with a suitable vehicle, e.g. sterile pyrogert-free water, before use.

The $GABA_B$ agonists may also be formulated in rectal compositions such as suppositories or retention enemas, e.g. containing conventional suppository bases such as cocoa butter or other glycerides.

The $GABA_B$ agonists may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the $GABA_B$ agonists may be formulated as solutions for administration via a suitable metered or unit dose device or alternatively as a powder mix with a suitable carrier for administration using a suitable delivery device.

Suitable dose ranges are described in the art, that is to say that for use as anti-emetics the compounds may be used at doses appropriate for other conditions for which $GABA_B$ agonists are known to be useful. It will be appreciated that it may be necessary to make routine variations to the dosage, depending on the age and condition of the patient, and the precise dosage will be ultimately at the discretion of the attendant physician or veterinarian. The dosage will also depend on the route of administration and the particular compound selected. A suitable dose range is for example 0.1 mg/kg to about 200 mg/kg bodyweight per day.

The $GABA_B$ agonists having an agonist action at $GABA_B$ receptors may, if desired, be administered in combination with one or more other therapeutic agents and formulated for administration by any convenient route in a conventional manner. Appropriate doses will be readily appreciated by those skilled in the art. For example, GABA agonists having an agonist action at $GABA_B$ receptors may be administered in combination with a systemic anti-inflammatory corticosteroid such as methyl prednisolone or dexamethasone, a $5HT_3$ antagonist such as ondansetron, granisetron or metoclopramide, or a tachykinin antagonist, including substance P antagonists and other neurokinin antagonists, such as an $NK_1$ receptor antagonist.

Biological Data

The anti-emetic activity of (±) baclofen was demonstrated by its ability to inhibit emesis induced by radiation, cisplatin, morphine and ipecacuanha in the ferret.

The anti-emetic activity of R(−) baclofen was demonstrated by its ability to inhibit radiation-induced emesis in the ferret.

Radiation Test

In this model of emesis the onset of retching and vomiting occurs approximately 20 minutes after whole body irradiation (2 Grey =200 Rads). The test compound is administered (e.g.i.p., p.o., i.v., s.c.) immediately after irradiation and its effect on emesis determined by comparison with appropriate controls.

(±) Baclofen inhibited emesis in the above test at 3 mg/kg p.o. and 1 mg/kg s.c. R(−) Baclofen inhibited emesis in the above test at 0.5 mg/kg s.c. S(+) Baclofen failed to inhibit emesis at 0.5 mg/kg s.c.

Cisplatin Test

In this model of emesis the onset of retching and vomiting occurs approximately 1 hour after the administration of cisplatin (200 mg/m² i.p.). The test compound was administered (s.c.) 1 hour after the administration of the emetogen and its effect on emesis determined by comparison with appropriate controls (e.g. water).

(±) Baclofen inhibited emesis in the above test at 1.0 mg/kg s.c.

(±) Baclofen inhibited ipecacuanha—and morphine-induced emesis in ferrets at 1.0 mg/kg s.c.

We claim:

1. A method for the treatment of emesis, which comprises administering to a mammal suffering from or susceptible to emesis an effective amount of a GABA agonist having an agonist action at $GABA_B$ receptors, with the proviso that when the emesis is caused by duodenal ileus, the GABA agonist is other than (±) baclofen.

2. A method according to claim 1 wherein the GABA agonist is baclofen.

3. A method according to claim 2 wherein the baclofen is administered in the form of buccal tablets.

4. A method according to claim 2 wherein the baclofen is administered parenterally.

5. A method according to claim 2 wherein the baclofen is formulated for depot or rectal administration.

6. A method according to claim 2 wherein the baclofen is in a form suitable for administration by inhalation or insufflation.

7. A method according to claim 2 wherein baclofen is in the R(−) form.

8. A method according to claim 1 wherein said emesis is induced by cancer chemotherapeutic agents, radiation sickness, radiation therapy, poisons, toxins, pregnancy, vestibular disorders, post-operative sickness, gastrointestinal obstruction, reduced gastrointestinal motility, visceral pain, migraine, increased intercranial pressure, decreased intercranial pressure, or opioid analgesics.

9. A method according to claim 8 wherein the GABA agonist is baclofen.

10. A method for the treatment of emesis, which comprises administering to a mammal suffering some or susceptible to emesis an effective amount of a GABA agonist having an agonist action at $GABA_B$ receptors, wherein said emesis is induced by a cancer chemotherapeutic agent, radiation sickness or radiation therapy.

11. A method according to claim 10 wherein said cancer chemotherapeutic agent is selected from the group consisting of cyclophosphamide, carmustine, lomustine, chloroambucil, dactinomycin, doxorubicin, mitomycin-C, bleomycin, cytarabine, methotrexate, 5-fluorouracil, etoposide, vinblastine, vincristine, cisplatin, decarbazine, procarbazine, hydroxyurea and combinations thereof.

12. A method according to claim 11 wherein the GABA agonist is baclofen.

13. A method according to claim 11 wherein said emesis is induced by cisplatin.

14. A method according to claim 11 wherein said emesis is induced by cyclophosphamide.

15. A method for the treatment of emesis, which comprises administering to a mammal suffering some or susceptible to emesis an effective amount of a GABA agonist having an agonist action at $GABA_B$ receptors, wherein said emesis is induced by morphine or ipecacuanha.

* * * * *